US009322927B2

(12) United States Patent
Lee et al.

(10) Patent No.: US 9,322,927 B2
(45) Date of Patent: Apr. 26, 2016

(54) FIBER-OPTIC SENSOR SYSTEM FOR MEASURING RELATIVE DOSE OF THERAPEUTIC PROTON BEAM BY MEASURING CERENKOV RADIATION AND METHOD OF MEASURING USING THE SAME

(75) Inventors: Bong Soo Lee, Seoul (KR); Kyoung Won Jang, Chungju-si (KR); Wook Jae Yoo, Gyeongju-Si (KR); Sang Hun Shin, Chungju-si (KR); Dong Ho Shin, Goyang-Si (KR)

(73) Assignee: Konkuk University Industrial Cooperation Corp., Seoul (KR)

( * ) Notice: Subject to any disclaimer, the term of this patent is extended or adjusted under 35 U.S.C. 154(b) by 0 days.

(21) Appl. No.: 14/415,055

(22) PCT Filed: Jul. 23, 2012

(86) PCT No.: PCT/KR2012/005862
§ 371 (c)(1),
(2), (4) Date: Jan. 15, 2015

(87) PCT Pub. No.: WO2014/017673
PCT Pub. Date: Jan. 30, 2014

(65) Prior Publication Data
US 2015/0168563 A1 Jun. 18, 2015

(51) Int. Cl.
*G01T 1/00* (2006.01)
*G01T 1/02* (2006.01)
(Continued)

(52) U.S. Cl.
CPC ............... *G01T 1/02* (2013.01); *A61N 5/1075* (2013.01); *G01T 1/22* (2013.01); *A61N 2005/1076* (2013.01); *A61N 2005/1087* (2013.01)

(58) Field of Classification Search
CPC .............. A61N 2005/1076; A61N 2005/1087; A61N 5/1075; G01T 1/02; G01T 1/22
USPC ........................................................ 250/393
See application file for complete search history.

(56) References Cited

U.S. PATENT DOCUMENTS 5,905,263 A * 5/1999 Nishizawa ........... A61N 5/1048
250/367
6,134,372 A * 10/2000 Ichikawa .............. G02F 1/3511
359/332
(Continued)

FOREIGN PATENT DOCUMENTS

JP H06294871 A 10/1994
JP H1082862 A 3/1998
(Continued)

OTHER PUBLICATIONS

Author: Bongsoo Lee et al., Title: Measurements of Relative Depth Doses Using Fiber-Optic Radiation Sensor and EBT Film for Brachytherapy Dosimetry, Date: Jun. 2010, Publisher: IEEE transactions on nuclear science, vol. 57.*
(Continued)

*Primary Examiner* — David J Makiya
*Assistant Examiner* — Taeho Jo
(74) *Attorney, Agent, or Firm* — Drinker Biddle & Reath LLP (57) ABSTRACT

The present invention relates to a fiber-optic sensor system for measuring the relative dose of a therapeutic proton beam by measuring Cerenkov radiation and a method of measuring using the same, and more particularly to a fiber-optic sensor system for precisely and economically measuring a proton beam by measuring the Cerenkov radiation generated from a fiber-optic sensor and a method of measuring using the same. The present invention comprises a proton beam source, a fiber-optic sensor for measuring the Bragg peak of the proton beam and SOBP, an optical detector for measuring the Cerenkov radiation, and a pair of optical fibers connecting the fiber-optic sensor and the optical detector, wherein the fiber-optic sensor being irradiated with a proton beam, the Cerenkov radiation generated in the optical fibers themselves is delivered through the optical detector to an amplifier system, and the resulting signal is transferred to a computer.

14 Claims, 7 Drawing Sheets

(51) Int. Cl.
*G01T 1/22* (2006.01)
*A61N 5/10* (2006.01)

(56) References Cited

U.S. PATENT DOCUMENTS

| | | | | |
|---|---|---|---|---|
| 2003/0163016 | A1* | 8/2003 | Testardi | A61N 5/1048 600/2 |
| 2004/0238749 | A1* | 12/2004 | Fontbonne | G01T 1/22 250/368 |
| 2009/0014665 | A1* | 1/2009 | Fleming | G01T 1/023 250/484.5 |
| 2011/0032600 | A1* | 2/2011 | Kondo | G02F 1/39 359/330 |
| 2011/0248188 | A1* | 10/2011 | Brusasco | A61N 5/1048 250/492.1 |
| 2012/0032080 | A1* | 2/2012 | Koyama | G02F 1/353 250/339.07 |
| 2012/0292517 | A1* | 11/2012 | Izaguirre | A61N 5/1071 250/362 |
| 2013/0236153 | A1* | 9/2013 | Rochette | G02B 6/2552 385/146 |
| 2014/0114150 | A1* | 4/2014 | Pogue | A61N 5/1075 600/317 |

FOREIGN PATENT DOCUMENTS

| | | |
|---|---|---|
| KR | 20090070541 A | 7/2009 |
| KR | 20120085499 A | 8/2012 |

OTHER PUBLICATIONS

International Search Report for PCT/KR2012/005862 mailed Mar. 11, 2013.

Jang, K.Y., et al, "Fabrication and Optimization of a Fiber-optic Dosimeter for Proton Beam Therapy Dosimetry", Korean Journal of Medical Physics, vol. 21, No. 1, (2010), pp. 29-34.

Jang, K.Y., et al, "Fiber-optic Cerenkov radiation sensor for proton therapy dosimetry", Optics Express, vol. 20, No. 13, (2012), pp. 13907-13914.

Jang, K.Y., et al, "Measurement of relative dose irradiated from a Co-60 source using a scintillating fiber-optic dosimeter", Journal of Korean Sensors Society, vol. 19, No. 1, (2010), pp. 52-57.

\* cited by examiner

FIBER-OPTIC SENSOR SYSTEM FOR MEASURING RELATIVE DOSE OF THERAPEUTIC PROTON BEAM BY MEASURING CERENKOV RADIATION AND METHOD OF MEASURING USING THE SAME

CROSS-REFERENCE TO RELATED APPLICATIONS

This application is a national stage application (under 35 U.S.C. §371) of PCT/KR2012/005862, filed Jul. 23, 2012, which is incorporated herein by reference in its entirety.

TECHNICAL FIELD

The present invention generally relates to a fiber-optic radiation sensor system for measuring a relative dose of a therapeutic proton beam based on the measurement of Cerenkov radiation and a measurement method using the system and, more particularly, to a fiber-optic radiation sensor system and a measurement method using the system, which are capable of more precisely and economically measuring a proton beam based on the measurement of Cerenkov radiation generated in a fiber-optic radiation sensor.

BACKGROUND ART

A fiber-optic radiation sensor (FORS) for measuring therapeutic radiation is generally composed of an organic scintillator and a plastic optical fiber. Due to such a configuration, upon measuring therapeutic radiation, an organic scintillator having a diameter of 1 mm or less, which is a water or tissue equivalent, is used. Thus, an FORS may reduce a correction task resulting from a difference in material from a phantom, may have high spatial resolution, and may be manufactured as a multi-dimensional sensor. Further, since an optical fiber is used, it is possible to perform long-range measurement in real time without interference from electromagnetic waves.

However, a common disadvantage of measuring devices that use a scintillator is a quenching effect, which may be applied even to fiber-optic radiation sensors.

Generally, if stopping power is low when a charged particle passes through a scintillator, the amount of scintillation occurring in the scintillator is proportional to the amount of energy lost in the charged particle, but if the stopping power is high, the amount of scintillation becomes close to a saturation state.

That is, when stopping power is high, a phenomenon in which the amount of scintillation occurring in the scintillator becomes out of proportion to the amount of lost energy of the charged particle is referred to as a "quenching effect."

Such an effect dearly appears upon measuring a high-energy proton beam using a scintillator.

Since stopping power at the Bragg peak of a proton beam is very high, a relative dose in the peak section of a proton beam is measured as a value lower than an actual value, upon performing measurement using the scintillator.

Therefore, the measurement of a high-energy proton beam using the scintillator requires a correction task using Birk's formula or the like.

Further, Cerenkov radiation generated in the optical fiber itself, other than the scintillator, due to a direct action between a glass or plastic optical fiber and a charged particle, has been reported as a problem in fiber-optic radiation sensors of existing inventions.

Cerenkov radiation, which denotes conically formed light having a predetermined angle with respect to an incident beam when a charged particle passes through a medium at a speed higher than the speed of light in the medium, is generated by a charged particle having a certain energy (in the case of a plastic optical fiber, electron: 170 keV, proton: 400 MeV) or more.

Therefore, when a dose is measured using a fiber-optic radiation sensor, it is dependent on the traveling direction and the emission intensity of a charged particle due to the emission angle of Cerenkov radiation and the length of an optical fiber to which the radiation is emitted.

However, since such Cerenkov radiation is a signal generated due to an interaction between radiation and a medium, it may be a significant signal upon measuring a relative dose if the emission angle and the length of the optical fiber to which radiation is emitted are fixed.

In particular, when the relative dose of a high-energy proton beam is measured using Cerenkov radiation generated in the optical fiber, a quenching effect attributable to the use of a scintillator may be eliminated, and thus there is an advantage in that a relative dose may be measured without requiring a special correction task.

Cerenkov radiation generated in an optical fiber by a therapeutic proton beam is generated by secondarily or tertiarily generated electrons without being directly generated due to the energy of the proton beam.

DISCLOSURE

Technical Problem

The present invention has been made keeping in mind the above problems, and an object of the present invention is to provide a fiber-optic radiation sensor system for measuring a relative dose of a therapeutic proton beam based on the measurement of Cerenkov radiation and a measurement method using the system, which utilize a subtraction scheme using a reference optical fiber so as to fix the length of an optical fiber to which a proton beam is emitted, measure Cerenkov radiation generated in the optical fiber having the fixed length depending on the depth of a water phantom, and then measure the Bragg peak and spread-out Bragg peak (SOBP) of the proton beam.

Technical Solution

The present invention includes a proton beam source, a fiber-optic radiation sensor for measuring a Bragg peak and a spread-out Bragg peak (SOBP) of a proton beam, a light measuring device for measuring Cerenkov radiation, and a pair of optical fibers for connecting the fiber-optic radiation sensor to the light measuring device, wherein when a proton is emitted to the fiber-optic radiation sensor, Cerenkov radiation generated in the pair of optical fibers themselves is transferred to an amplifier system through the light measuring device, and a final signal is transmitted to a computer.

Further, the optical fibers may be glass or plastic optical fibers and may be configured to generate Cerenkov radiation when a high-energy charged particle is emitted.

Furthermore, the light measuring device may be implemented using a charge coupled device (CCD), a photodiode, a photomultiplier tube (PMT), or the like.

Furthermore, the proton beam source may emit a high-energy therapeutic proton beam generated by a cyclotron.

The present invention includes, in a method measuring Cerenkov radiation generated in optical fibers by a therapeutic proton beam source, (a) preparing a proton beam source generated by a cyclotron, (b) sensing a Bragg peak and a spread-out Bragg peak (SOBP) of a proton beam from the proton beam source by measuring Cerenkov radiation generated in a fiber-optic radiation sensor, (c) performing light measurement and photomultiplication required for measurement of Cerenkov radiation through a light measuring device, and d) transferring the Cerenkov radiation to an amplifier system through the light measuring device, allowing the Cerenkov radiation to be amplified, and transmitting a final signal to a computer through an electric signal measuring device.

Further, at the (b), optical fibers may be glass or plastic optical fibers and may be configured to generate Cerenkov radiation when a high-energy charged particle is emitted.

Furthermore, at the (c), the light measuring device may be implemented using a charge-coupled device (CCD), a photodiode, a photomultiplier tube (PMT), or the like.

Furthermore, the proton beam source may emit a high-energy therapeutic proton beam generated by a cyclotron.

Advantageous Effects

In accordance with the present invention having the above configuration, there is an advantage in that a relative dose of a therapeutic proton beam may be more precisely and economically measured by means of significant Cerenkov radiation.

BEST MODE

Hereinafter, details for practicing the present invention will be described in detail with reference to the attached drawings.

In the present invention, Cerenkov radiation generated in optical fibers due to a therapeutic proton beam is measured.

In order to fix the lengths of optical fibers to which Cerenkov radiation is emitted, a subtraction scheme using a reference optical fiber is applied to the present invention. Cerenkov radiation generated in optical fibers 30 having a fixed length is measured depending on the depth of a water phantom and then the Bragg peak and spread-out Bragg peak (SOBP) of the proton beam are measured. Such measurement results are compared with the results of measurement in an ionization chamber.

Further, in order to compare the results of measurement of Cerenkov radiation with the results of a typical fiber-optic radiation sensor (FORS) including a scintillator, experiments for measuring the Bragg peak and SOBP of a proton beam are performed using a fiber-optic radiation sensor.

Figure 1:
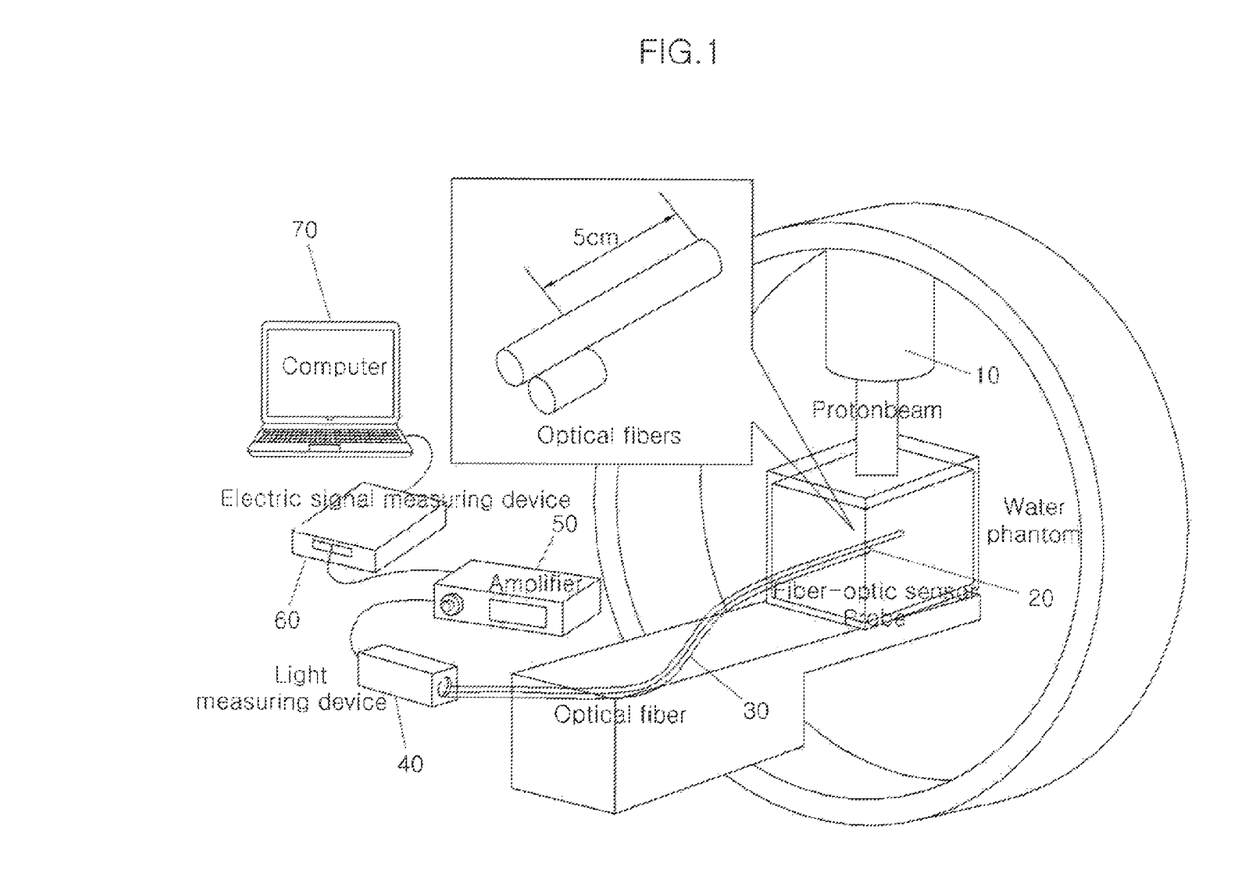
FIG. 1 is a diagram showing experimental configuration for measuring Cerenkov radiation generated in optical fibers depending on the depth of a water phantom according to the present invention.

As shown in FIG. 1, a system for measuring a relative dose of a therapeutic proton beam based on the measurement of Cerenkov radiation according to the present invention chiefly includes a proton beam source 10; a fiber-optic radiation sensor 20 for measuring the Bragg peak and SOBP of a proton beam from the proton beam source 10; a light measuring device 40 for measuring Cerenkov radiation, and optical fibers 30 for connecting the fiber-optic radiation sensor 20 to the light measuring device 40, Therefore, when a proton is emitted to the fiber-optic radiation sensor 20, the Cerenkov radiation generated in the fiber-optic radiation sensor 20 is transferred to an amplifier system through the light measuring device 40, and a final signal is transmitted to a computer 70 via an electric signal measuring device 60.

The fiber-optic radiation sensor 20 and the optical fibers 30 are glass or plastic optical fibers and are configured to generate Cerenkov radiation when a high-energy charged particle is emitted.

For comparative experiments, a scintillator used to manufacture a fiber-optic radiation sensor is an organic scintillator made of a plastic material.

The light measuring device 40 is implemented using a charge-coupled device (CCD), a photodiode, a photomultiplier tube (PMT) or the like.

Figure 3:
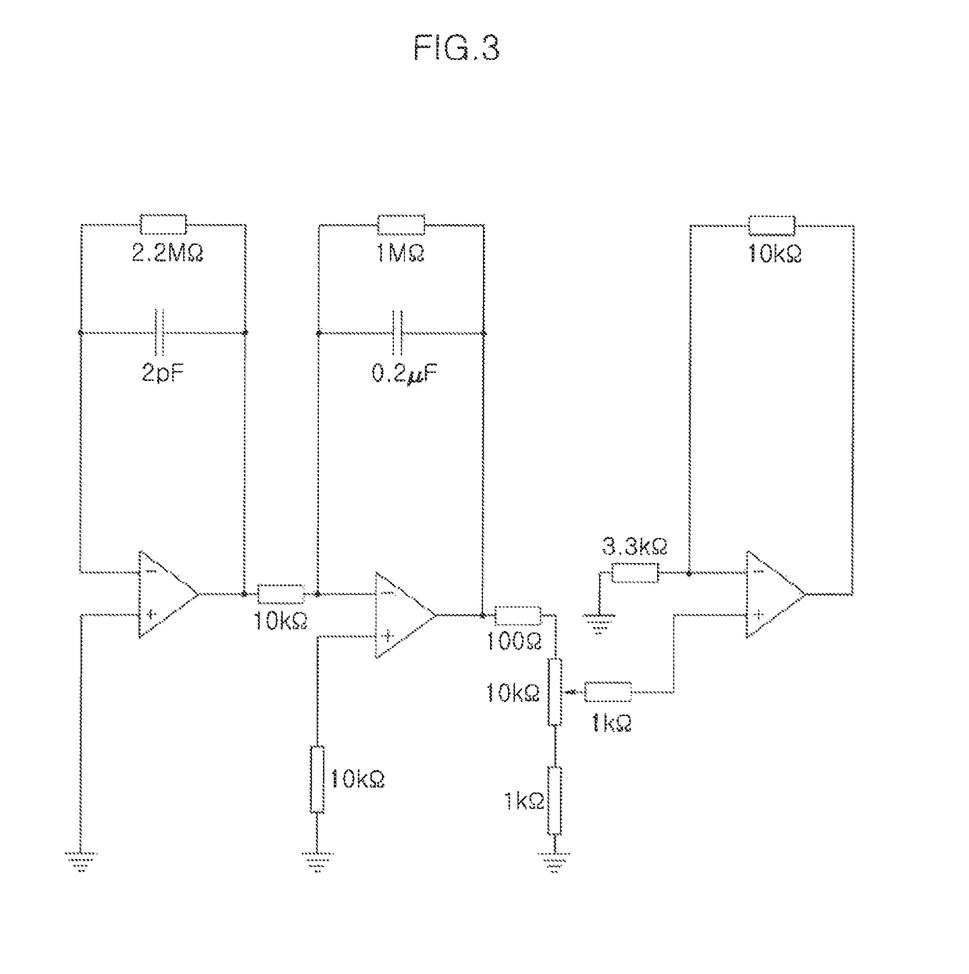
FIG. 3 is a circuit diagram showing a separately manufactured amplifier system to amplify an electrical signal generated in a photomultiplier tube according to the present invention.

A separately manufactured amplifier system is used to amplify an electrical signal generated by the light measuring device 40, and a circuit diagram of the amplifier system is illustrated in FIG. 3.

The proton beam source 10 emits a high-energy therapeutic proton beam generated by a cyclotron.

Figure 2:
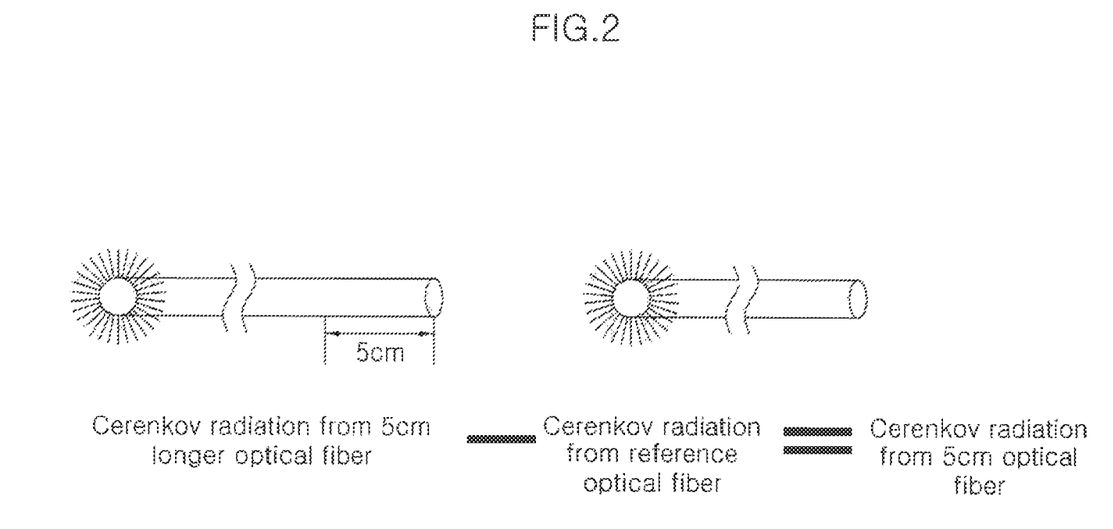
FIG. 2 is a diagram showing the principle of a subtraction scheme fir measuring Cerenkov radiation generated in optical fibers having a fixed length according to the present invention.

FIG. 2 illustrates the principle of a subtraction scheme for measuring Cerenkov radiation generated in optical fibers 30 having a fixed length.

Therefore, when a proton is emitted using an optical fiber 30 longer than a reference optical fiber by 5 cm, Cerenkov radiation generated in an optical fiber corresponding to a length of 5 cm may be measured using a difference between Cerenkov radiations generated in the two optical fibers 30.

As can be seen in FIG. 1, when protons are emitted to the optical fibers 30, Cerenkov radiation generated in the optical fibers 30 themselves is transferred to the light measuring device 40 and the amplifier system 50 through the optical fiber 30 having a length of 15 m, and a final signal is transmitted to a computer via an electric signal measuring device.

Hereinafter, a method for measuring a relative dose of a therapeutic proton beam based on the measurement of Cerenkov radiation to practice the present invention will be described in detail, and the results of measurement will be analyzed.

The method for measuring a relative dose of a therapeutic proton beam based on the measurement of Cerenkov radiation according to the present invention relates to a method for measuring Cerenkov radiation generated in optical fibers by a therapeutic proton beam source, and includes the first step of preparing a proton beam source generated by a cyclotron; the second step of sensing the Bragg peak and SOBP of a proton beam from the proton beam source by measuring Cerenkov radiation generated by a fiber-optic radiation sensor; the third step of performing light measurement and photomultiplication required for the measurement of Cerenkov radiation using a light measuring device; and the fourth step of transferring the Cerenkov radiation to an amplifier system through the light measuring device, allowing the Cerenkov radiation to be amplified, and transferring a final signal to a computer through an electric signal measuring device.

Figure 4:
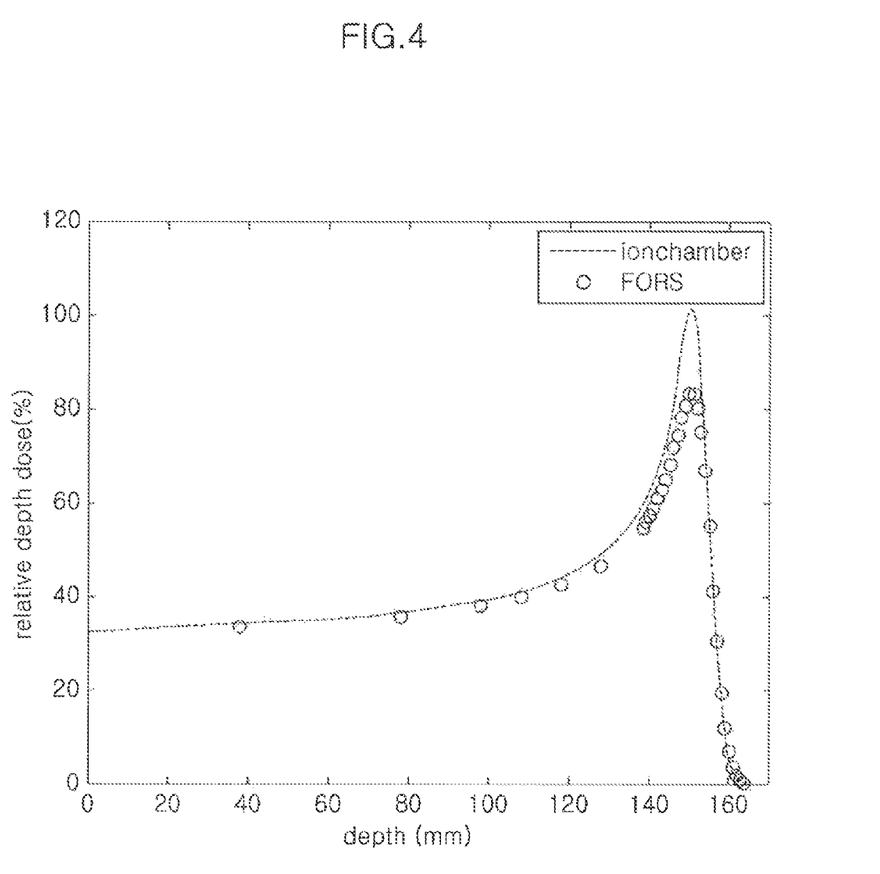
FIGS. 4 and 5 are diagrams showing the results of measuring the Bragg peak and spread-out Bragg peak (SOBP) of a 180 Melt/proton beam using a typical fiber-optic radiation sensor (FORS) including a scintillator according to the present invention.
Figure 5:
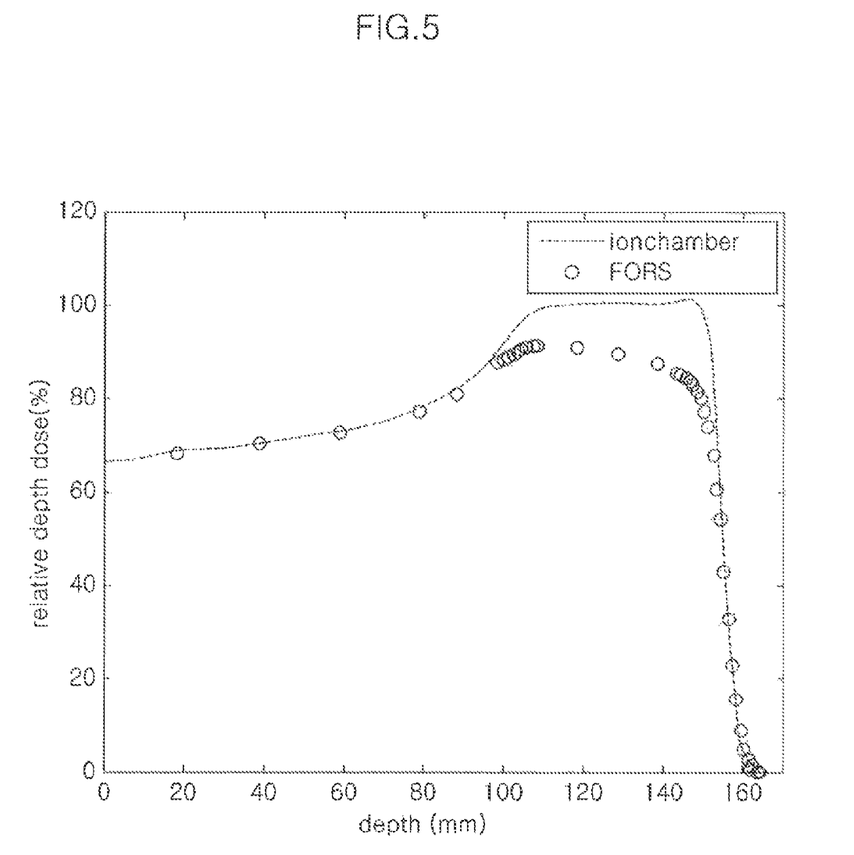

FIGS. 4 and 5 based on the above-described method for measuring a relative dose of a therapeutic proton beam based on the measurement of Cerenkov radiation illustrate the results of measuring the Bragg peak and SOBP of a 180 MeV proton beam by using a typical fiber-optic radiation sensor including a scintillator.

Referring to the measurement results, it can be seen that a relative dose in a peak section is measured as a low value due to the quenching effect of the scintillator.

Further, FIG. 4 illustrates the results of measuring the Bragg peak of the proton beam, wherein a difference from the results of measurement obtained by an ionization chamber in the peak section is about 20%.

FIG. 5 illustrates the results of measuring the SOBP of the proton beam using a fiber-optic radiation sensor. Generally, SOBP overlaps Bragg peaks of various proton beams having different energy regions to maintain a uniform dose in a limited range.

Since the quenching effects of the scintillator differ for proton beams having different energy regions, a predetermined slope appears in the peak section when the SOBP of the proton beams is measured using the typical fiber-optic radiation sensor including the scintillator. The results of the fiber-optic radiation sensor in the peak section of the SOBP exhibit a difference of about 10 to 20% from the results of the ionization chamber.

Figure 6:
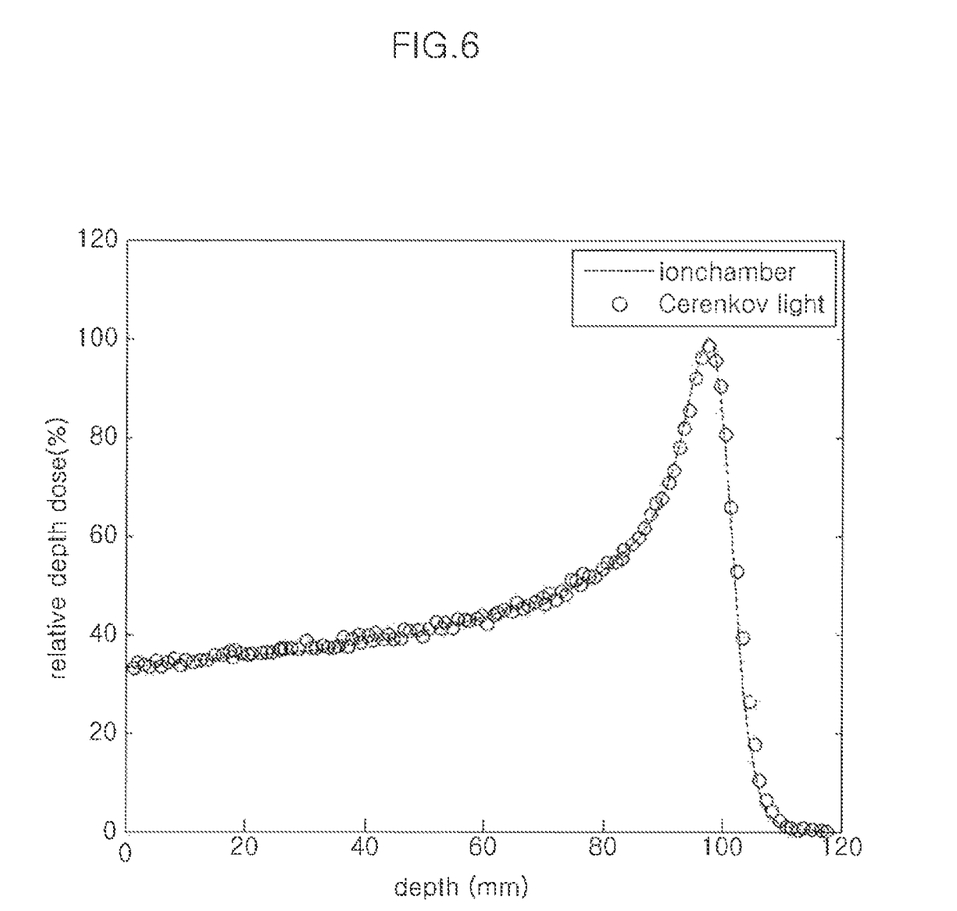
FIGS. 6 and 7 are diagrams showing the results of measuring the Bragg peak and SOBP of the proton beam depending on the depth of a water phantom based on the measurement of Cerenkov radiation according to the present invention.
Figure 7:
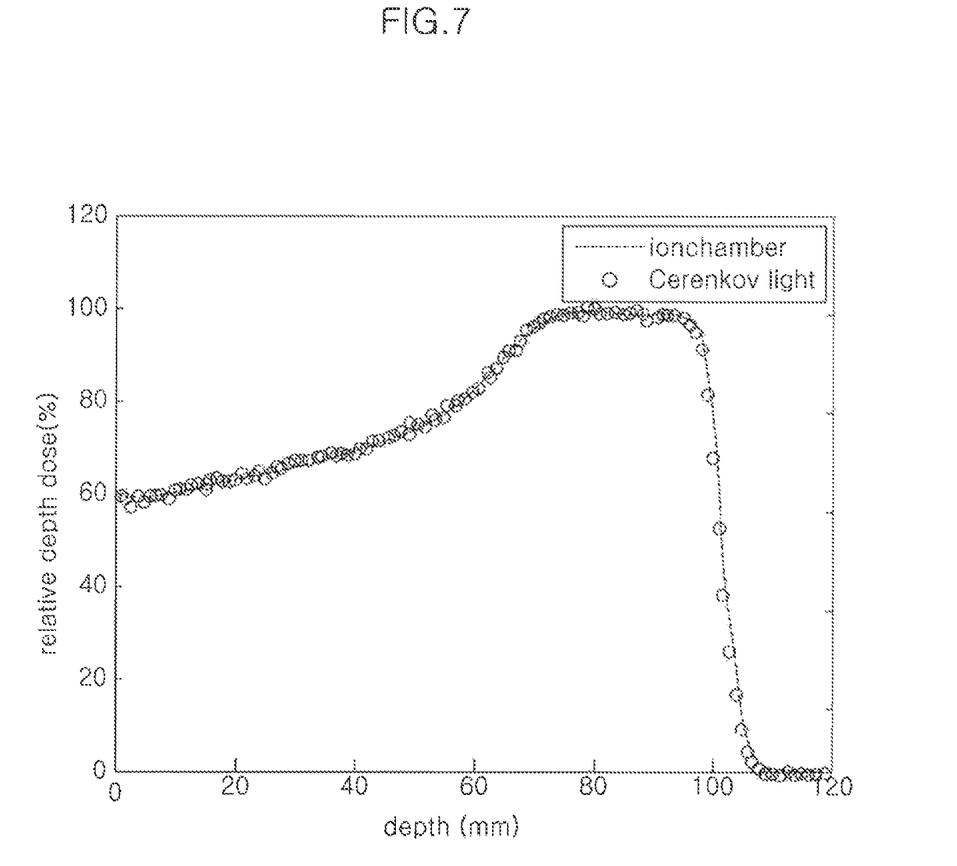

FIGS. 6 and 7 illustrate the results of measuring the Bragg peak and SOBP of a proton beam depending on the depth of a water phantom based on the measurement of Cerenkov radiation.

FIG. 6 illustrates the results of measuring the Bragg peak of a 173 MeV proton beam. using Cerenkov radiation generated by the fiber-optic radiation sensor. It can be seen in FIG. 6 that a maximum value is obtained at a position of about 100 mm, which is a maximum dose point.

Further, the relative dose measured using Cerenkov radiation exhibits a tendency to be almost identical to that of the ionization chamber, and has a difference of about 1.9% at the maximum dose point.

FIG. 7 illustrates the results of measuring the SOBP of a proton beam using Cerenkov radiation. It can be seen in FIG. 7 that a uniform dose section is exhibited in a range from about 75 to 95 mm.

As the results of measuring the SOBP of the proton beam using Cerenkov radiation generated by the fiber-optic radiation sensor, it can be seen that the SOBP is almost identical to that of the ionization chamber and has a difference of about 0.7% in a maximum dose section.

The invention claimed is:

1. A fiber-optic radiation sensor system comprising:
a proton beam source emitting a high-energy therapeutic proton beam;
a pair of optical fibers for being emitted by the proton beam, wherein the pair of optical fibers have different lengths at one ends of the pair of optical fibers;
a fiber-optic radiation sensor for generating Cerenkov radiation by the emitted proton beam, wherein the one ends of the pair of optical fibers are fixed inside the fiber-optic radiation sensor; and
a light measuring device for detecting the Cerenkov radiation to measure a Bragg peak and a spread-out Bragg peak (SOBP) of the proton beam, wherein the other ends of the pair of optical fibers are connected to the light measuring device.

2. The fiber-optic radiation sensor system of claim 1, wherein the optical fibers are glass or plastic optical fibers and are configured to generate the Cerenkov radiation when a high-energy charged particle is emitted.

3. The fiber-optic radiation sensor system of claim 1, wherein the light measuring device is any one of a charge-coupled device (CCD), a photodiode, and a photomultiplier tube (PMT).

4. The fiber-optic radiation sensor system of claim 1, wherein the sensor system further comprises:
an amplifier system for generating a final signal by amplifying a signal of the light measuring device generated by the Cerenkov radiation; and
a computer for measuring a relative dose of the proton beam based on the final signal.

5. The fiber-optic radiation sensor system of claim 1, wherein the different lengths at the one ends of the pair of optical fibers in the fiber-optic radiation sensor are fixed using a subtraction scheme based on a reference optical fiber.

6. The fiber-optic radiation sensor system of claim 5, wherein the one ends of the pair of optical fibers in the fiber-optic radiation sensor are composed of the reference optical fiber and an optical fiber which is about 5cm longer than the reference optical fiber.

7. The fiber-optic radiation sensor system of claim 1, wherein the Bragg peak and the SOBP are measured by measuring the Cerenkov radiation depending on a depth of a water phantom.

8. A method for measuring Cerenkov radiation, comprising:
(a) emitting a high-energy therapeutic proton beam to a pair of optical fibers having different lengths at one ends of the pair of optical fibers with a proton beam source;
(b) generating Cerenkov radiation by the emitted proton beam with a fiber-optic radiation sensor which the one ends of the pair of optical fibers are fixed inside the fiber-optic radiation sensor; and
(c) detecting measuring the Cerenkov radiation to measure a Bragg peak and a spread-out Bragg peak (SOBP) of the proton beam with a light measuring device which the other ends of the pair of optical fibers are connected to the light measuring device.

9. The method of claim 8, wherein the optical fibers are glass or plastic optical fibers and are configured to generate the Cerenkov radiation when a high-energy charged particle is emitted.

10. The method of claim 8, wherein the light measuring device is any one of a charge-coupled device (CCD), a photodiode, and a photomultiplier tube (PMT).

11. The method of claim 8, wherein the method further comprises:
(d) generating a final signal by amplifying a signal of the light measuring device generated by the Cerenkov radiation with an amplifier system; and
(e) measuring a relative dose of the proton beam based on the final signal with a computer.

12. The method of claim 8, wherein the different lengths at the one ends of the pair of optical fibers in the fiber-optic radiation sensor are fixed using a subtraction scheme based on a reference optical fiber.

13. The method of claim 12, wherein the one ends of the pair of optical fibers in the fiber optic radiation sensor are composed of the reference optical fiber and an optical fiber which is about 5 cm longer than the reference optical fiber.

14. The method of claim 8, wherein the Bragg peak and the SOBP are measured by measuring the Cerenkov radiation depending on a depth of a water phantom.

\* \* \* \* \*